United States Patent [19]

Michaeli

[11] 4,117,141
[45] Sep. 26, 1978

[54] METHOD OF INHIBITING FLEA-BITE ALLERGY

[76] Inventor: Dov Michaeli, 1431 8th Ave., San Francisco, Calif. 94122

[21] Appl. No.: 770,101

[22] Filed: Feb. 18, 1977

[51] Int. Cl.$^2$ .......................................... A61K 31/415
[52] U.S. Cl. .............................................. 424/273 R
[58] Field of Search ........................................ 424/273

[56] References Cited

PUBLICATIONS

Merck Index–eighth edit. (1968) pp. 33, 286 and 532.
Cox–Chem. Abst., vol. 80 (1974) p. 87514u.

*Primary Examiner*—Sam Rosen
*Attorney, Agent, or Firm*—Limbach, Limbach & Sutton

[57] ABSTRACT

A method of inhibiting the allergic reaction to flea bites by hyposensitizing the host with free allantoin or allantoin derivatives. Allantoin serves to neutralize the antibody in the bloodstream specific to flea-bite antigen. It also serves to neutralize B-lymphocytes to arrest the cloning process necessary to formation of antibody.

9 Claims, No Drawings

METHOD OF INHIBITING FLEA-BITE ALLERGY

BACKGROUND OF THE INVENTION

This invention relates to inhibiting flea-bite allergy by hyposensitizing the host. Allantoin has been found to influence the allergic response.

Allantoin has been used for many years for the treatment of dermatological affections. A summary of its emollient uses is contained in "Allantoin and Aluminum Derivatives in Dermatological Application", Lubowe, and Mecca, Drug and Cosmetic Industry, January 1959: 84, 1, page 36. Numerous patents exist relating to dermatological applications of allantoin and its derivatives.

The emollient properties of allantoin are non-specific. The biochemical basis for the anti-irritant, keratolytic and healing properties of allantoin is still unknown. The prior art fails to recognize any specific action against flea bite allergy.

It has also been known to administer flea extract to hosts sensitive to flea bite allergy in an effort to inhibit the allergic response. However, the allantoin contained in flea extract is complexed to high molecular weight protein carrier. It is the allantoin - protein complex which induces the immune response, so that the administration of flea extract fails to effectively inhibit the allergy.

SUMMARY OF THE INVENTION

Free allantoin or allantoin derivatives which are not complexed to a carrier inhibit flea bite allergic reaction by hyposensitizing the host. Humans and animals can be protected against development of allergic reaction to flea bites over a sustained period of time.

I have found that the saliva of fleas contains allantoin bound to a high molecular weight protein carrier. The allergic response to flea-bite is believed to be as follows. By biting the host, fleas inject antigen consisting of allantoin and carrier into the blood stream of the host. There the antigen induces B-lymphocyte cells, developed in bone marrow, to synthesize and secrete antibody. The B-lymphocytes are stem cells which reproduce by cloning to rapidly develop a substantial number in the body of the host. Each B-lymphocyte has receptor sites on its surface adapted to bind selectively with allantoin, the haptene complexed with the carrier to form the antigen.

After the induction of antibody, further introduction of flea-bite antigen produces the allergic response. The allantoin/carrier antigen injected by the flea binds immediately with antibodies to form antigen/antibody complexes. The antigen/antibody complex damages the surrounding tissue by histaminic response and other mediators of inflammatory response which are toxic to cells.

According to the present invention, I have discovered that many molecules of allantoin are complexed to the carrier protein to form the antigen. The antibody is divalent and can bind to two allantoin sites on the protein complex to form a lattice of antibody bound to protein complex through allantoin "bridges". The large lattice molecule triggers the irritating reactions of flea-bite allergy.

The present invention consists of injecting free allantoin into the bloodstream of the host. If the host has been previously bitten by a flea, the induction of antibodies will have taken place and B-lymphocytes are present specifically adapted to bind to allantoin. The free allantoin binds both valence sites of the antibody and neutralizes it, thereby precluding the formation of a large lattice-work complex of antigen/antibody.

The neutralization of antibody provides a short-term benefit from the invention, but continued production of antibody ultimately overcomes all allantoin present. The cloning process of the B-lymphocyte stem cell proceeds until plasma cells are formed to end the process. The plasma cells circulate in the blood stream and have the same specificity as the B-lymphocyte clones to recognize the allantoin haptenic shape.

The long-term benefit of the invention is to bind free allantoin to the receptor sites of the stem cell to preclude binding to antigen. By neutralizing the receptor sites of the B-lymphocyte with free allantoin, the cloning process is arrested. This is because T-lymphocytes, formed in the thymus gland, bind with the protein carrier of the antigen and excrete a stimulant to the B-lymphocytes to commence the cloning process. Because the high molecular weight carrier is not bound to the allantoin present by this invention, there is no binding to the T-lymphocyte and, consequently, no stimulant to the cloning process. This second level of protection resulting from the presence of free allantoin provides immune tolerance to flea-bite allergy.

DESCRIPTION OF THE PREFERRED EMBODIMENT

For purposes of this application, the term "haptenic allantoin" shall be defined as free allantoin having the chemical formula:

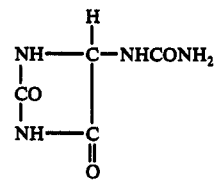

or low molecular weight combinations of allantoin such as Allantoin N-Acetyl-DL-Methionine, Aluminum Hydroxy Allantoin N-Acetyl-DL-Methionine, Aluminum Chlorhydroxy Allantoin N-Acetyl-DL-Methionine, Aluminum Allantoinates, Bismuth Allantoinates, Allantoin-Formaldehyde Condensation product and silver Allantoinates. Examples of suitable salts are indicated in U.S. Pat. No. 2,761,867. Other materials may be combined with allantoin so long as the additives do not promote cell destruction and histaminic release. Preferably, the molecular weight of such additives should be below 1,000 to receive full benefits of the invention. Small peptides, having a molecular weight below 1,000, will not alter the therapeutic effect of allantoin against flea bite allergy when combined in a suitable preparation. However, high molecular weight materials, such as proteins, polymers and polysaccharides, should be avoided. Proteins in particular appear to have a strong affinity for allantoin.

It is preferred that the molecular weight of any additive materials to be combined with allantoin be less than 1,000 to avoid the inflammatory response when combined with the antibodies in the host. Peptide chains having a molecular weight under 1,000 are suitable, so long as the beneficial effects of allantoin are not inhibited. However, high molecular weight materials, such as proteins, complex polysaccharides and other polymers should be avoided. Proteins, in particular, appear to strongly bind to allantoin, thereby minimizing the haptenic effect of free allantoin. As a result, combinations of allantoin with protein actually hypersensitize, rather than hyposensitize.

Haptenic allantoin is conveniently administered in aqueous solution. A practical minimum amount is 0.05%, and the maximum percentage is the limit of solubility. It has been found convenient to use allantoin in a 0.5% solution.

For injection into the bloodstream, a phosphate-buffered saline solution may conveniently be used. For example, into 125 ml of distilled water there may be added between 0.1 and 1.5 grams of NaCl. While not essential, up to 1 gram of KCl may also be added. Buffering is conveniently accomplished by $Na_2HPO_4$ and/or $KH_2PO_4$ in any desired combination to give a pH between the range of 5 and 9.

EXAMPLE I

A 0.5% solution of allantoin in phosphate-buffered saline solution containing 1% sodium alginate was prepared, as described below. The following salts were dissolved in 125 ml of distilled water:

| | |
|---|---|
| NaCl | 1 gm |
| KCl | 0.025 gm |
| $Na_2HPO_4$ | 0.176 gm |
| $KH_2PO_4$ | 0.02 gm |
| 0.5 ml of 100% liquified phenol was added as a preservative (final concentration 0.49 volume for volume). | |

To this buffer solution 1.25 gm. sodium alginate (final concentration 1% weight per volume) was added with stirring until completely dissolved. Allantoin, 0.625 gm (final concentration 0.5% weight per volume) was then added and stirred while dissolved. The mixture was filtered and sterilized and then placed in a vial and kept in a refrigerator until use.

The addition of sodium alginate prior to addition of allantoin is designed to enhance the latter's solubility. Addition of allantoin to phosphate buffer without sodium alginate results in a saturated solution of approximately 0.6 mg/ml.

The preferred sustained release agent is sodium alginate. However, other water soluble salts of alginic acid are highly satisfactory for this purpose. Also, I have found that Freund's Adjuvant is satisfactory for the purpose of releasing the allantoin gradually over a relatively long period of time. Other materials known to cause slow and sustained release, e.g. Pertussis vaccine, should also prove satisfactory for this purpose.

Dogs or cats were injected subcutaneously in several sites along the back and sides. Each injection site received 1.0 ml. The usual dose was 2 mg/kg body weight, but lower doses, e.g. 0.5 mg/kg, were found to be also effective. Conversely, for an animal that is extremely hypersensitive or is refractory to the usual dose, larger doses of allantoin, e.g. 5-10 mg/kg body weight can be administered. With human beings, the dose of allantoin injected should be the same as in other animals, namely approximately 0.5-5.0 mg/kg body weight.

Treatment should be repeated as required, depending upon the sensitivity of the host and the likelihood of exposure to flea bites. In some areas of the country the exposure to flea bites is confined to certain months of the year. I have found that a convenient and effective schedule is three weekly injections. This schedule resulted in hyposensitization of approximately 70% of the treated dogs and cats for periods of at least 3 months, and lasting as long as 1 year.

Administration of allantoin for reducing sensitivity to flea bite allergy may be carried out in any suitable manner except topically or intraveneously. Ordinarily, slow release vehicles are inoperative for reagents administered intravenously or topically. For oral administration, or for injection, microencapsulation of allantoin is a suitable means of administration.

Where salts of allantoin are used, the solubility of allantoin will vary. There is no limit on the concentration of allantoin to be administered and ordinarily a saturated solution is prepared so that concentration depends upon the solubility of the salt.

To minimize irritation to the patient, it is preferred to have the pH of the solution near 7. Suitable buffers, such as phosphate buffer, may be used to adjust the pH as necessary. The pH is not critical, but should be within 2 pH units of 7 to avoid annoyance to the animal.

Where gradual release of other therapeutic agents is desired on approximately the same schedule as the release of allantoin, combination of allantoin with other agents is acceptable, so long as there is no inhibition of the desired effects of allantoin release. By way of example, corticosteroids may be included in the allantoin preparation for their anti-inflammatory effect. Thus, the scratching that frequently accompanies the allergic response to flea bites may be alleviated at the same time the hyposensitization is taking place. Corticosteroids are non-specific and help to stabilize mast cells to limit the pouring out of histamine and other inflammatory mediators.

EXAMPLE II

Various corticosteroids, for example, hydrocortisone, methylprednisolone, or dexamethasone, can be administered in combination with allantoin. For example, the following preparation can be used: The following ingredients were dissolved in 125 ml distilled water.

NaCl — 0.800 gm
KOH — 0.225 gm
$Na_2HPO_4$ — 0.176 gm
$KH_2PO_4$ — 0.02 gm
Phenol — 0.5 ml of 100% solution
Sodium alginate — 1.25 gm
Allantoin — 0.625 gm
Hydrocortisone sodium succinate ester — 2.500 gm This combination allows the administration of approximately 1.7 mg allantoin and 7.0 mg hydrocortisone per kg body weight.

I found that allantoin can be administered as a food additive or dissolved in drinking water, and offers specific protection against allergy to flea bites. A typical example is the incorporation of 100 mg allantoin in the daily intake of dog or cat food. Alternatively, a 0.1 - 0.5 mg/ml solution of allantoin in drinking water is also effective in hyposensitization to flea bites.

Because flea bite allergy is associated with histaminic response, it is appropriate to combine allantoin with anti-histamines.

EXAMPLE III

To the preparation described in Example I, compounds with antihistaminic action can be added. For example, diphenylhydramine hydrochloride can be added to an allantoin preparation so that a total dose of 5 - 10 mg/kg body weight is delivered.

A typical preparation consists of the following ingredients dissolved in 125 ml of distilled water:

NaCL — 0.500 gm
KCl — 0.525 gm
Na$_2$HPO$_4$ — 0.176 gm
KH$_2$PO$_4$ — 0.02 gm
0.5 ml of 100% liquified phenol
Sodium alginate — 1.25 gm
Allantoin — 0.500 gm
Diphenylhydramine — 1.875 gm Diphenylhydramine can be substituted with other compounds with antihistaminic properties. For example, chlorpheniramine at 4.687 gm/125 ml of allantoin preparation will result in delivery of 10 - 20 mg/kg body weight of the compound. Alternatively, promethazine hydrochloride at 375 mg/125 ml of allantoin preparation will result in delivery of 1 - 2 mg/kg body weight.

I claim:

1. A method of hyposensitizing the allergic reaction in a host to flea-bite comprising injecting an effective amount of allantoin or allantoin derivatives subcutaneously into a host and repeating the injection during the period of exposure of the host to fleas.

2. A method of hyposensitizing the allergic reaction in a host to flea-bite comprising the steps of mixing allantoin or allantoin derivatives with a sustained release vehicle, injecting an effective amount of the mixture subcutaneously into a host, gradually hyposensitizing the host by neutralizing antibodies to flea antigen in the host.

3. A method as in claim 2 wherein the sustained release vehicle is a water-soluble salt of alginic acid.

4. A method of hyposensitizing the allergic reaction in a host to flea-bite comprising orally administering an effective amount of allantoin or allantoin derivatives to a host and repeating the administration during the period of exposure of the host to fleas.

5. A method as in claim 4 wherein the allantoin or allantoin derivatives is mixed with a sustained release vehicle.

6. A method of hyposensitizing the allergic reaction in a host to flea-bite comprising administering an effective amount of allantoin or allantoin derivative mixed with antihistamine until hyposensitization takes place.

7. A method of hyposensitizing the allergic reaction in a host from flea-bite, comprising the administration of an effective amount of allantoin or allantoin derivative mixed with corticosteroids until hyposensitization takes place.

8. A composition of matter comprising an aqueous solution for injection, an effective amount of allantoin or allantoin derivative for hyposensitizing the allergic reaction in a host to flea-bite and a corticosteroid.

9. A composition of matter comprising an aqueous solution for injection, an effective amount of allantoin or allantoin derivative for hyposensitizing the allergic reaction in a host to flea-bite and a compound with antihistaminic action.

* * * * *